United States Patent [19]

Toms et al.

[11] 4,269,196

[45] May 26, 1981

[54] PEDIATRIC TIDAL VOLUME INDICATOR AND VENTILATOR ADAPTATION

[76] Inventors: Norman D. Toms, P.O. Box 70, Argyle, Manitoba; Jules O. Legal, 89 Elm Park Rd., Winnipeg, Manitoba, both of Canada

[21] Appl. No.: 892,838

[22] Filed: Apr. 3, 1978

[30] Foreign Application Priority Data

Apr. 5, 1977 [GB] United Kingdom ............... 14337/77

[51] Int. Cl.³ .............................................. A61B 5/08
[52] U.S. Cl. ............................... 128/727; 128/205.23; 128/205.24
[58] Field of Search ........ 128/2.08, 2.07, 145.5–145.8, 128/DIG. 29, 725–729, 203.12, 205.23, 205.24

[56] References Cited

U.S. PATENT DOCUMENTS

| 3,395,699 | 8/1968 | Beasley | 128/2.08 |
|---|---|---|---|
| 3,527,205 | 9/1970 | Jones | 128/2.08 |
| 3,559,639 | 2/1971 | Nagus et al. | 128/2.08 |
| 3,820,539 | 6/1974 | Ollivier | 128/145.8 |
| 3,961,624 | 6/1976 | Weigl | 128/2.08 |
| 3,967,619 | 7/1976 | Story et al. | 128/145.8 |
| 4,121,581 | 10/1978 | Schmeder | 128/145.8 |

Primary Examiner—Lee S. Cohen
Attorney, Agent, or Firm—Stanley G. Ade

[57] ABSTRACT

The tidal volume indicator consists of a spirometer in conjunction with a ventilator system adapted for use for small children and neonates. The ventilator system incorporates valving to segregate the component parts into a machine system and a patient system and includes a unidirectional check valve between the exhalation valve manifold and the patient system. The tidal volume indicator includes a spirometer with read-out amplifier operatively connected therewith which enables the volume to be read accurately from between, for example, 0 and 150 ml. It consists of a rack and pinion assembly connected to the vertically moving shaft of the spirometer and a volume indicator needle in conjunction with the necessary scale. Also included is an adjustable warning operating device which will actuate an alarm or indicator if the preset volume deviates by a predetermined amount.

10 Claims, 7 Drawing Figures

4,269,196

PEDIATRIC TIDAL VOLUME INDICATOR AND VENTILATOR ADAPTATION

BACKGROUND OF THE INVENTION

This invention relates to new and useful improvements in pediatric tidal volume indicators together with adaptations and improvements to ventilators making them particularly adaptable for use with the tidal volume indicator.

Conventional spirometers can be used for measuring small volumes by collecting, for example, ten breaths and averaging. This provides the ability to measure 10 ml. volumes which is accomplished by adding a shut-off valve in the spirometer dump valve power line.

However, it is desirable to provide a system of read-out giving breath by breath monitoring of exhaled tidal volumes and this requires a form of amplification to the read-out of the conventional spirometer.

SUMMARY OF THE INVENTION

By adapting a ventilator to pediatric use and connecting same to a spirometer having a read-out amplifier on the spirometer, single breath indicated volumes can be indicated which are accurate to the extent normally required.

One aspect of the invention consists of the improvement in a pediatric tidal volume indicator and ventilator system used therewith, said tidal volume indicator comprising a spirometer and read-out amplifier operatively connected to said shaft, selective means operatively connecting said ventilator to said spirometer, said ventilator system including means to segregate same into a machine system and a patient system whereby, upon inspiration, said spirometer is isolated from said patient system, and upon exhalation, said machine system is isolated from said patient system and said patient system is operatively connected to said spirometer, said means including a unidirectional check valve between said systems, one side of said unidirectional check valve being connected to said machine system, the other side of said unidirectional check valve being connected to said patient system. The machine system of said ventilator system includes a source of gas under pressure and a first exhalation valve assembly operatively connected to said source and to said one side of said unidirectional check valve. The patient system of said ventilator system includes a circle tubing component comprising an inspiratory arm and an expiratory arm with an airway bifurcation connecting one end of each of said arms together. The other end of said inspiratory arm is operatively connected to the other side of said unidirectional check valve. The selective means operatively connecting said ventilator system to said spirometer includes a second exhalation valve assembly operatively extending between the other end of said expiratory arm and said spirometer and the second exhalation valve assembly is operatively connected to said source of gas under pressure.

With the foregoing in view, and other advantages as will become apparent to those skilled in the art to which this invention relates as this specification proceeds, our invention consists essentially in the arrangement and construction of parts all as hereinafter more particularly described, reference being had to the accompanying drawings in which:

DESCRIPTION OF THE DRAWINGS

FIG. 6 is an enlarged partially sectioned view of the adjusting nut assembly.

FIG. 7 is a schematic view of the alarm setting control.

In the drawings like characters of reference indicate corresponding parts in the different figures.

DETAILED DESCRIPTION

Figure 5:
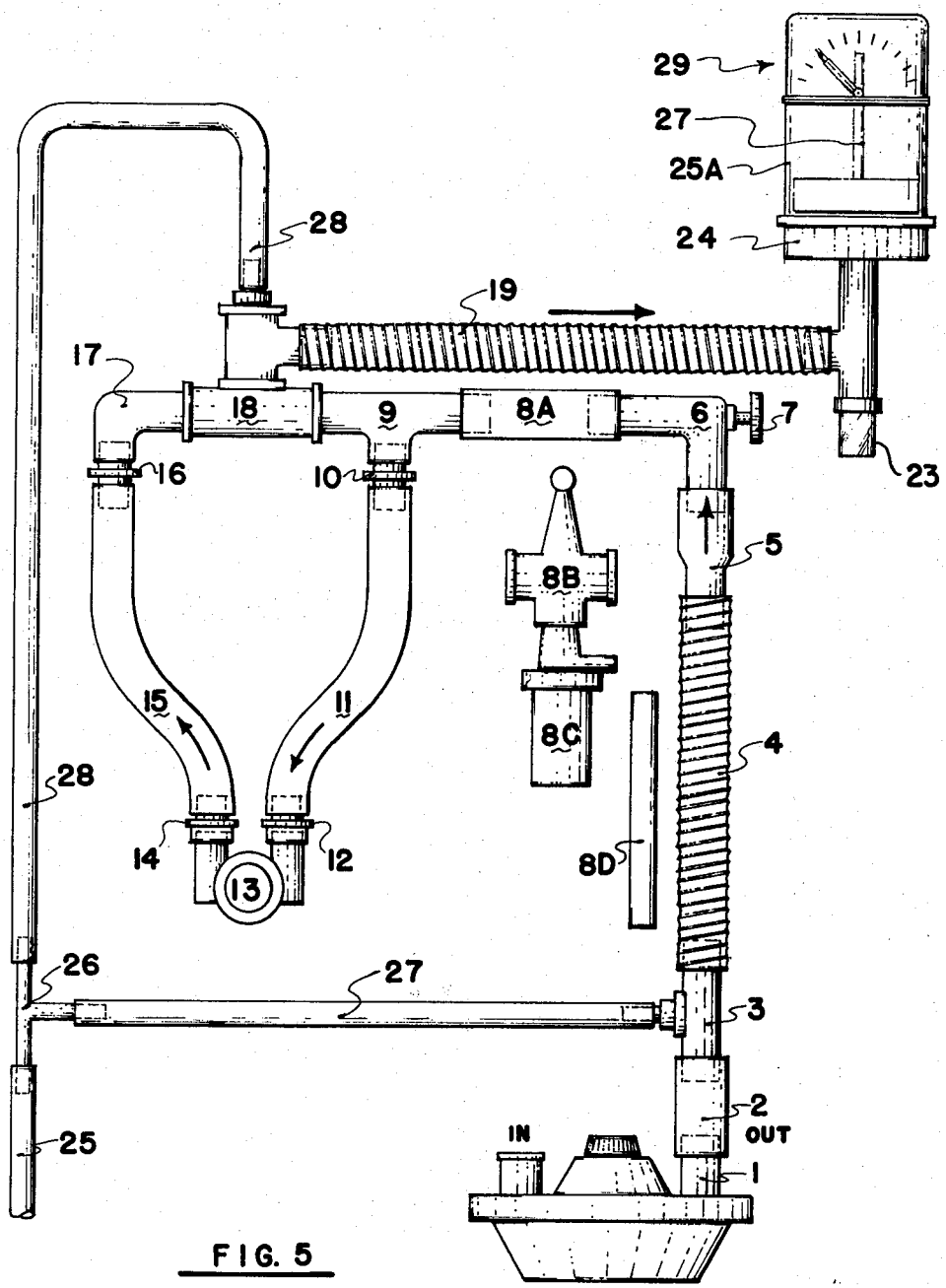
FIG. 5 is an exploded schematic view of a conventional ventilator adapted to pediatric use and including the improvement forming part of the invention.

Dealing first with the ventilator improvements, reference should first be made to FIG. 5. This shows a circle system configuration adapted from a conventional pediatric set, in this instance, a Bennett MA-1 pediatric set. However, other pediatric sets can be used.

the system is particularly useful in patients of the small infant to child size (that is, ventilating of patients with predicted ventilation volumes of from 50 to 100 ml).

In preliminary experiments, volumes were monitored by accumulating a total of 10 breaths exhaled by the patient and averaged to derive single breath values. This system of averaging worked reasonably well, but with the advent of a sigh mode in therapy as an accepted procedure in order to assist in preventing peripheral collapse of the lungs, it has become essential to look at individual single breaths.

Figure 4:
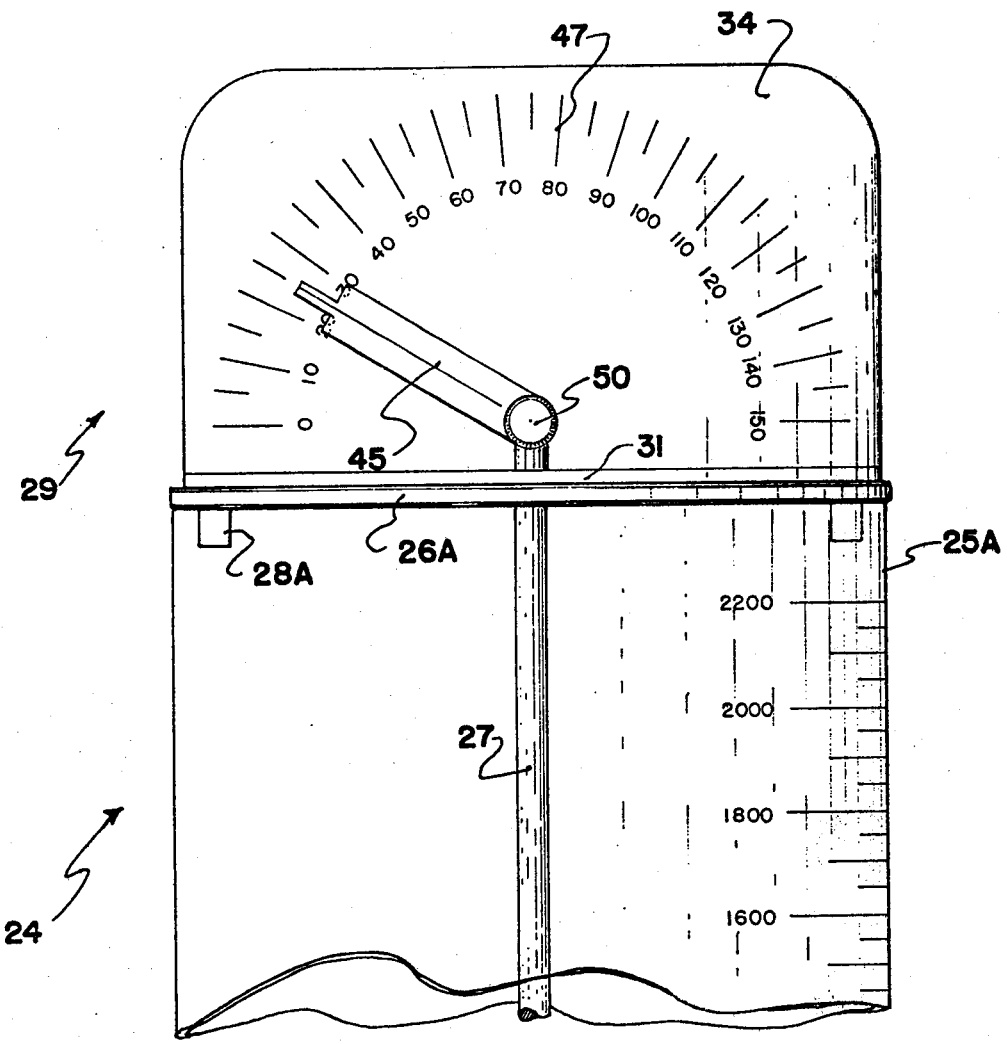
FIG. 4 is a partial view of a conventional spirometer bell with the invention secured to the upper side thereof.

Conventional spirometers such as the Bennett spirometer, are designed for adults and have minimum increments of 100 ml. in a short scale interval (see FIG. 4). Normal ventilating volume for adults is between 500 and 1000 ml. so that such scales are adequate.

However, with children including neonates, the volume may be between 10 to 100 ml. so that a normal spirometer is not usable, inasmuch as the movements are too small to measure accurately even if another scale was used.

Because of this, a mechanical amplifier has been designed which will hereinafter be described, in order to read out the small displacement volumes exhaled into the bellows of a spirometer which, in this instance, is a Bennett monitoring spirometer. A novel pneumatic circuit configuration will also be described. However, any other conventional type of spirometer can readily be adapted for use with the amplifier herein and the pneumatic circuit configuration.

This gives the capability of adapting a low volume alarm which will produce an audible sound with visual indication, if desired. The low volume alarm may be triggered if the exhaled volume does not come within a specific time period. In this particular application, the alarm may be triggered if the exhaled volume does not come within 5 ml. of the preset volume within a specific time. There is also an alarm shut-off switch which is provided with a visual indicator when it is in the OFF position. Means for initiating the alarm is included in the structure.

The system is beneficial in providing a more meaningful approach to the assessment of the adequacy of patient ventilation, but without the volume indicator now being utilized, these changes are not readily visualized. Small but clinically significant changes in volume can occur due to minor leaks around the endotracheal tube (a common problem with pediatric patients who are unable to use a tube with an inflatable cuff).

In a conventional system, there is a system compliance and compressibility factor of approximately 3 ml./cm. $H_2O$. That is to say, if a ventilating pressure of 30 cm $H_2O$ is required to provide adequate ventilation of a patient, $30 \times 3 = 90$ ml. of gas is ventilating the system and does not enter the patient's lungs.

During exhalation, when the exhalation valve is opened to release the pressure from the system, the 90 ml. and the volume exhaled from the patient's lung enters the spirometer; the spirometer thus over-reads the ventilating volume.

If this factor is applied to a patient requiring 50 ml. to ventilate adequately, it would indicate a volume of 90 and $50 = 140$ ml. indicated and this gives a very gross and inaccurate indication of the adequacy of the ventilation of this patient, which indication is normally unacceptable.

Therefore, in the present invention, the system is segregaged into two groups of component parts namely, the machine system—3.0 ml/cm $H_2O$ and the patient system—0.4 ml/cm $H_2O$.

In FIG. 5, as shown schematically, a Cascade (T.M.) humidifier with thermostatic temperature control is indicated by reference character 1 and in this instance, a Bennett Cascade humidifier is used. To this is attached a silastic adapter 2 connected in turn to a straight exhalation valve manifold 3, which in this instance includes a gas collector, silastic adapter and check valve on outflow, all of which comprises a first exhalation valve assembly. This provides for a more consistent sensitivity of the machine-to-patient respiratory effort.

Relatively non-distensible corrugated tubing 4 extends from the exhalation valve manifold to a unidirectional check valve 5 which separates the machine system from the patient system and which, together with valve 3, forms a novel feature of this invention.

The patient system includes a thermometer manifold 6 connected to the check valve 5 and having a thermometer 7 operatively connected thereto. A straight connector adapter 8A connects to the manifold 6 and if desired, an alternate nebulizer system 8B and 8C, together with compressed gas power line 8D, may be provided for use with broncho-dilator therapy.

An inspiratory elbow 9 connects to the connector 8A and an adapter 10 for the circle tubing connects to one side of the elbow 9. This inspiratory arm 11 of the circular tubing connects in turn to a further adapter 12 and to the proximal airway bifurcation 13 which is the connection to the patient's endotracheal tube. For convenience and to maintain the integrity of the circle tubing assembly, the elbow 9 is also joined to one side of the exhalation valve manifold 18, but no gas connection is present at this point.

A further adapter 14 connects the airway bifurcation 13 to the expiratory arm 15 of the circle tubing and in turn is connected via adapter 16 to the expiratory elbow 17. This connects to a straight exhalation valve manifold 18 with gas collector to gather exhaled gases. This manifold 18 and the gas collector comprise a second exhalation valve assembly.

In operation, on inspiration, both exhalation valve assemblies 3 and 18 are closed, sealing the system. This closing is by pneumatic gas line 25 and 28 with take-off tee 26 and connector 27. Line 25 extends from the machine.

Pressure then builds up in the system with the volume of air required to provide adequate air entry for the patient and this air passes through the circuit and some volume is lost in the circuit while some enters the patient's lungs.

At the end of inspiration, both exhalation valves 3 and 18 are opened, by reverse of pressure in lines 25 and 28, allowing gases to flow from the system so that the gases in the patient's lungs plus those in the patient system leave the circuit through exhalation valve assembly 18 to the spirometer collectively designated 24.

Conducting tube 19 extends from the exhalation valve manifold 18 to a connector and condensate bottle 23 and thence to the spirometer 24.

The gases in the machine circuit leave the system through the exhalation or dump valve 3 via the gas collector valve manifold and unidirectional valve to atmosphere and there can be no back-flow from the patient circuit due to the check valve 5. This permits the necessary accuracy required for small children and neonates, and provides complete control of $CO_2$ (from re-breathing), thus giving precise control of inspired gas values.

FIGS. 1 to 4 inclusive show details of the improvement to the spirometer 24 which in this instance, is a Bennett monitoring spirometer of a positive displacement type. It includes the outer bell 25A through which the central shaft 27 of the spirometer passes. In the top of the bell 25A, a plurality of apertures are provided (not illustrated). Locating plugs or pegs 28A extend downwardly from the base adapter 26A of the indicator assembly thus locating the indicator assembly securely upon the upper end of the spirometer bell.

Figure 1:
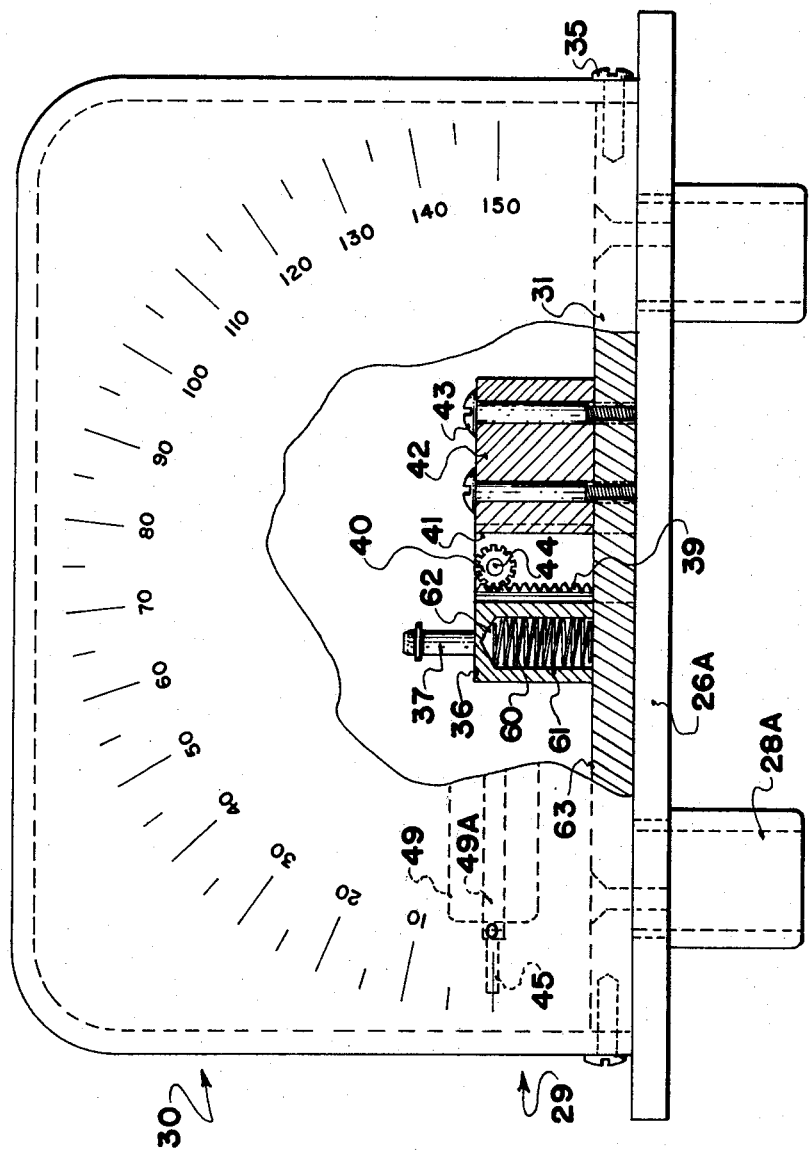
FIG. 1 is a front elevation of the pediatric spirometer indicator per se, broken away in part and sectioned substantially along the line 1—1 of FIG. 2.
Figure 2:
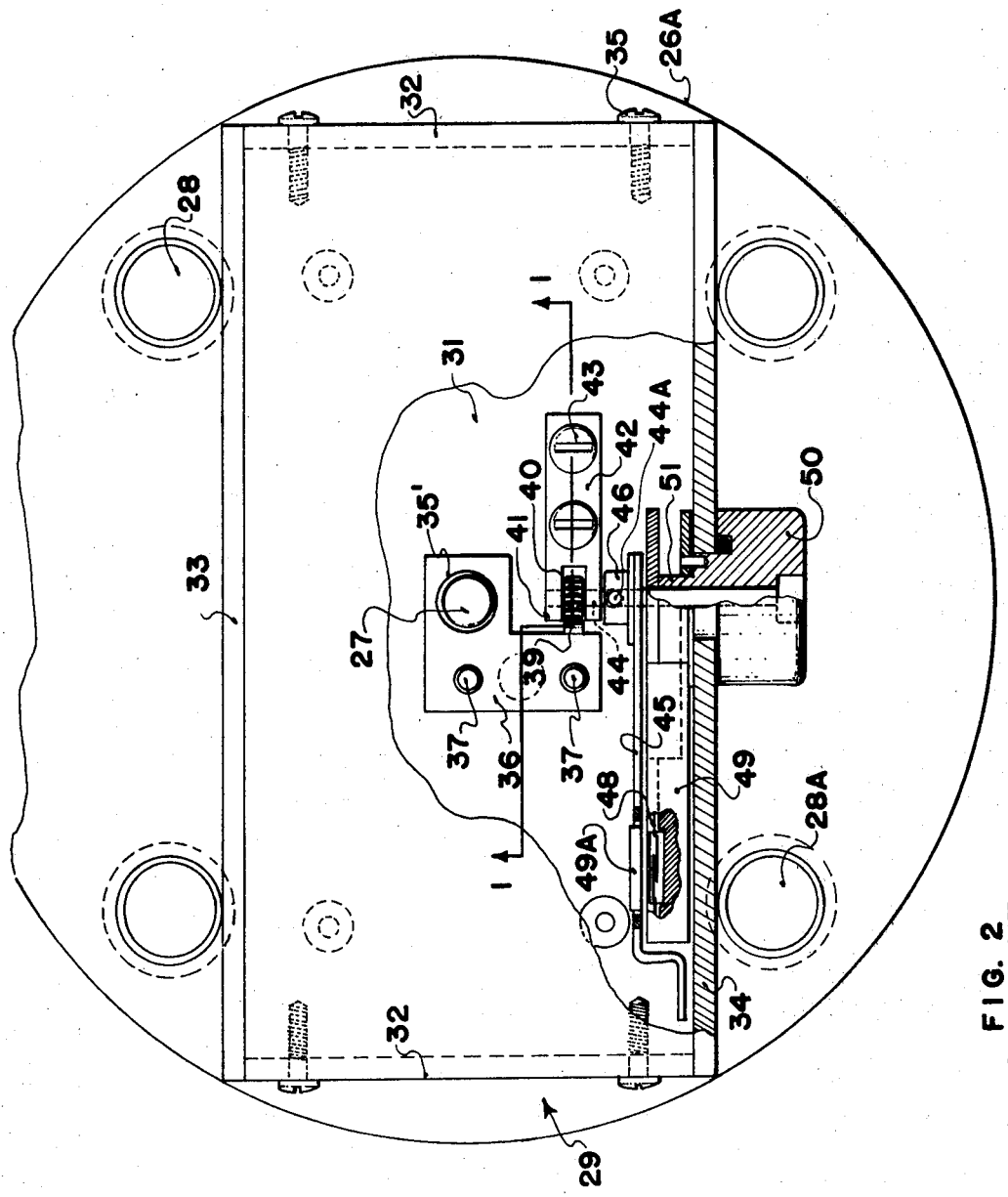
FIG. 2 is a top plan view of FIG. 1 also broken away in part to show the interior thereof.
Figure 3:
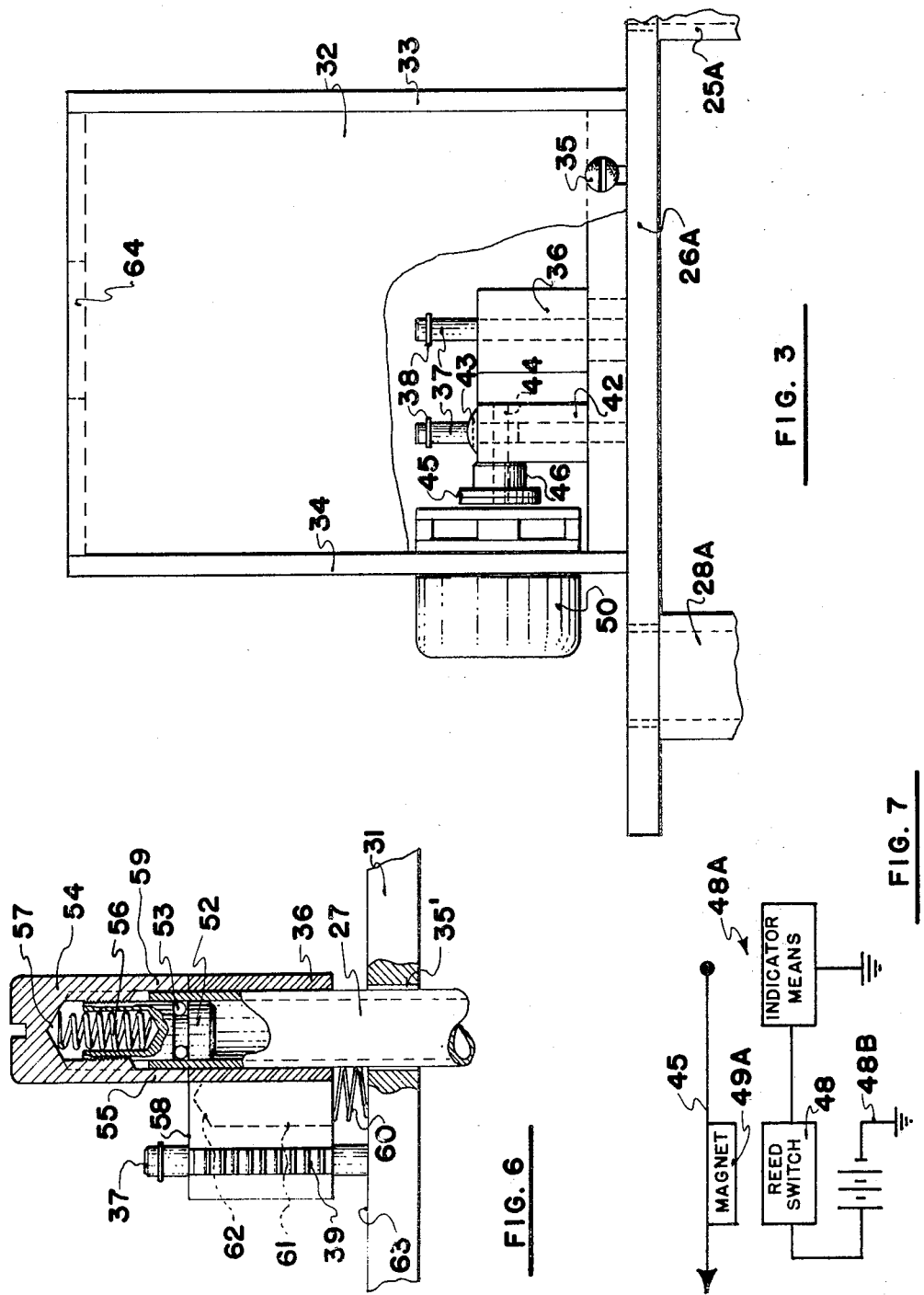
FIG. 3 is an end elevation of FIG. 1 broken away in part to show the interior thereof.

The indicator assembly collectively designated 29, is shown in detail in FIGS. 1, 2 and 3. It comprises a casing collectively designated 30, and preferably manufactured from transparent synthetic plastic material. The casing includes a base 31, side panels 32, rear panel 33 and front panel 34, all secured together or moulded as a unit so that the various panels or surfaces form the enclosure within which the mechanism is located. The enclosure 30 is secured to the base 31 by means of screws 35. However, other methods of forming the enclosure can be used as can other securements to the base 31.

The aforementioned vertically moving shaft 27 of the spirometer extends upwardly into the casing through a circular aperture 35' formed within the base and a rack block 36 engages over the shaft as shown in FIG. 6. The rack block 36 is mounted for free sliding vertical movement upon a pair of cylindrical posts 37 extending upwardly from the base with clips 38 limiting the upward movement of the rack block.

The rack block includes vertical rack 39 formed thereon engageable with a mating gear or pinion 40 which is journalled for rotation within the bifurcated ends 41 of a gear mount 42 which in turn is secured to the base 31 by means of screws 43. The gear 40 is secured to a shaft 44 which is journalled for rotation transversely, within bifurcated ends 41 of the mount 42 and this shaft extends towards the front cover or panel 34 and is provided with a volume indicator needle 45 secured to hub 46 which in turn is secured to shaft 44 by means of set screw 44A or the like (see FIG. 2). This needle moves behind the transparent front panel 34 bearing indicating indicia 47 thereon as clearly shown in FIG. 1.

A conventional reed switch assembly collectively designated 48 is mounted on an alarm setting control 49 including a manually operated knob 50, on the front panel 34, mounted upon shaft 51 which also carries the control 49.

Actuator magnet 49A for the reed switch assembly is mounted on indicator needle 45. Parameters are so chosen that switch assembly 48 is actuated when the magnet 49A comes within a preselected operating distance of the reed switch (for example, a distance equivalent to 5 ml.).

Electric leads extend from the reed switch assembly 48 to a suitable alarm circuit 48A including a source of power 48B which will provide an audible, visual or remote control alarm, in the event that the patient ventilating volume falls below a level set by the control 49, for more than a preselected time interval. This alarm circuit is preferably electronic utilizing presently available components.

The operator adjusts the setting by control knob 50 depending upon the requirements of the particular patient.

The ratio between the rack 39 and the gear 40 gives the necessary amplification of the movement of the vertical shaft 27 of the spirometer so that the volume can be read accurately, in this instance, between 0 and 150 ml.

FIG. 6 shows details of the attachment of the rack block 36 to the aforementioned vertically moving shaft 27 of the spirometer. The rack block 36 slides freely on the upper end of shaft 27 which is provided with a cylindrical nut adapter 52 engageable within the hollow upper end of shaft 27 and is held in position frictionally by means of an O-ring 53 surrounding the adapter.

A portion of this adapter 52 extends above the upper end of shaft 27 and is screw threaded externally to receive an adjustment nut 54 which includes a lower shroud portion 55 freely engageable over the upper end of the shaft or tube 27. A small coil spring 56 engages between the adapter 52 and the upper interior side 57 of the nut providing frictional tension to the threads in order to prevent the nut from turning inadvertently once it has been preset manually.

The upper side 58 of the rack block 36 engages the underside 59 of the nut 54 and the rack block is maintained in engagement with this underside by the provision of a further coiled spring 60 mounted within a cylindrical bore 61 formed upwardly from the base of the rack block and reacting between the upper end 62 of this bore and the upper surface 63 of the base plate 31.

This means that as the spirometer guide tube or shaft 27 moves up and down due to the action of the spirometer, the rack block 36 is maintained in contact with the underside of nut 54 unless the spirometer guide tube moves upwardly sufficient to enable the upper side 58 of the rack block to engage the aforementioned clips 38 on the posts 37. Under these circumstances, the spirometer guide tube freely rises and in this connection, an aperture 64 is provided at the top of the casing 30. This may occur if a volume greater than 150 ml. enters the spirometer and prevents any damage from occurring to the spirometer.

It will be appreciated that as soon as the volume returns to a level below 150 ml., the tube 27 lowers and the nut 54 once again engages the upper surface 58 of the rack block 36 so that measurements below 150 ml. are readable.

The nut 54 is used to adjust the zero position of the needle 45 prior to attaching the spirometer.

It will also be appreciated that this arrangement permits the spirometer to be used normally without having to disconnect the attachment secured thereto.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. An improvement in a pediatric tidal volume indicator and ventilator system used therewith comprising in combination, a spirometer, a vertically moving shaft in said spirometer and a read-out amplifier operatively connected to said shaft, selective means operatively connecting said ventilator system to said spirometer, said ventilator system including means to segregate same into a machine system and a patient system whereby, upon inspiration, said spirometer is isolated from said patient system, and upon exhalation, said machine system is isolated from said patient system and said patient system is operatively connected to said spirometer, said means to segregate including a unidirectional check valve between said systems, one side of said unidirectional valve being connected to said machine system, the other side of said unidirectional valve being connected to said patient system, said machine system of said ventilator system including a source of gas under pressure, and a first exhalation valve assembly operatively connected to said source and to said one side of said unidirectional check valve, said patient system of said ventilator system including a circle tubing component comprising an inspiratory arm and an expiratory arm, an airway bifurcation connecting one end of each of said arms together, the other end of said inspiratory arm being operatively connected to said other side of said unidirectional check valve, said selective means operatively connecting said ventilator system to said spirometer including a second exhalation valve assembly operatively extending between the other end of said expiratory arm and said spirometer and said second exhalation valve assembly being operatively connected to said source of gas under pressure.

2. The improvement according to claim 1 in which said read-out amplifier includes a casing and means to support said casing upon the upper side of said spirometer with the upper end of said vertically moving shaft entering said casing, a rack and pinion assembly in said casing including a rack block freely movable vertically on said shaft and means in said casing for guiding and limiting the upward movement of said rack block vertically, means to journal said pinion for rotation within said casing, an indicator needle operatively connected to said pinion and indicia means in said casing swept by said indicator needle.

3. The improvement according to claim 2 which includes means to adjustably mount the rack block upon said shaft, said last mentioned means including means to adjust the relative relationship between said rack block and said shaft thereby enabling limited adjustment of said indicator needle relative to said indicia means, for zeroing purposes, and spring means for maintaining said rack block in contact with said means to adjustably mount said rack block upon said shaft, prior to said rack block reaching the upper limit of movement thereof, said shaft being enabled to move freely upwardly when said block reaches the said limit of movement thereof.

4. The improvement according to claim 3 which includes an adjustable alarm setting control in said casing, indicating means operatively connected to said control, said alarm setting control including a reed switch assembly adjustably positioned adjacent the sweep of said indicator needle, and magnetic means mounted on said indicator needle for operating said reed switch and hence said indicating means, when said magnetic means comes within a predetermined distance from said reed switch, and a source of power operatively connected to said reed switch and said indicating means.

5. The improvement according to claim 2 which includes an adjustable alarm setting control in said casing, indicating means operatively connected to said control, said alarm setting control including a reed switch assembly adjustably positioned adjacent the sweep of said indicator needle, and magnetic means mounted on said indicator needle for operating said reed switch and hence said indicating means, when said magnetic means comes within a predetermined distance from said reed switch, and a source of power operatively connected to said reed switch and said indicating means.

6. A read-out amplifier for a spirometer which includes the vertically moving shaft, said read-out amplifier including a casing and means to support said casing upon the upper side of said spirometer with the upper end of said vertically moving shaft entering said casing, a rack and pinion assembly in said casing including a rack block freely movable vertically on said shaft and means in said casing for guiding and limiting the upward movement of said rack block vertically, means to journal said pinion for rotation within said casing, an indicator needle operatively connected to said pinion and indicia means in said casing swept by said indicator needle.

7. A read-out amplifier according to claim 6 which includes means to adjustably mount the rack block upon said shaft, said last mentioned means including means to adjust the relative relationship between said rack block and said shaft thereby enabling limited adjustment of said indicator needle relative to said indicia means, for zeroing purposes, and spring means for maintaining said rack block in contact with said means to adjustably mount said rack block upon said shaft, prior to said rack block reaching the upper limit of movement thereof, said shaft being enabled to move freely upwardly when said block reaches the said limit of movement thereof.

8. A read-out amplifier according to claim 6 which includes an adjustable alarm setting control in said casing, indicating means operatively connected to said control, said alarm setting control including a reed switch assembly adjustably positioned adjacent the sweep of said indicator needle, and magnetic means mounted on said indicator needle for operating said reed switch and hence said indicating means, when said magnetic means comes within a predetermined distance from said reed switch, and a source of power operatively connected to said reed switch and said indicating means.

9. The read-out amplifier according to claim 7 which includes an adjustable alarm setting control in said casing, indicating means operatively connected to said control, said alarm setting control including a reed switch assembly adjustably positioned adjacent the sweep of said indicator needle, and magnetic means mounted on said indicator needle for operating said reed swtich and hence said indicating means, when said magnetic means comes within a predetermined distance from said reed switch, and a source of power operatively connected to said reed switch and said indicating means.

10. A ventilator system for use with a spirometer or the like, said ventilator system comprising in combination selective means for connecting said ventilator system to the spirometer, said ventilator system including means to segregate same into a machine system and a patient system whereby, upon inspiration, said spirometer is isolated from said patient system, and upon exhalation, said machine system is isolated from said patient system and said patient system is operatively connected to said spirometer, said means including a unidirectional check valve between said systems, one side of said unidirectional valve being connected to said machine system, the other side of said unidirectional valve being connected to said patient system, said machine system of said ventilator system including a source of gas under pressure, and a first exhalation valve assembly operatively connected to said source and to said one side of said unidirectional check valve, said patient system of said ventilator system including a circle tubing component comprising an inspiratory arm and expiratory arm, an airway bifurcation connecting one end of each of said arms together, the other end of said inspiratory arm being operatively connected to said other side of said unidirectional check valve, said selective means for operatively connecting said ventilator system to said spirometer including a second exhalation valve assembly operatively extending between the other end of said expiratory arm and said spirometer and said second exhalation valve assembly being operatively connected to said source of gas under pressure.

* * * * *